US005859326A

United States Patent [19]
An

[11] Patent Number: 5,859,326
[45] Date of Patent: Jan. 12, 1999

[54] GENE CONTROLLING FLORAL DEVELOPMENT AND APICAL DOMINANCE IN PLANTS

[75] Inventor: Gynheung An, Pullman, Wash.

[73] Assignee: Washington State University, Pullman, Wash.

[21] Appl. No.: 323,449

[22] Filed: Oct. 14, 1994

[51] Int. Cl.$^6$ .............................. A01H 5/00; C12N 15/29; C12N 5/04; C12N 15/82
[52] U.S. Cl. ........................ 800/205; 435/69.1; 435/70.1; 435/172.3; 435/240.4; 435/320.1; 536/23.6; 536/24.3
[58] Field of Search .................................. 536/23.6, 24.3; 435/69.1, 70.1, 172.3, 320.1, 240.4; 800/205

[56] References Cited

PUBLICATIONS

Matsuoka et al., 1993. Plant Cell 5:1039–1048.
Coupland, "LEAFY Blooms in Aspen," *Nature* 377:482–483 (1995).
Weigel et al., "A Developmental Switch Sufficient for Flower Initiation in Diverse Plants," *Nature* 377:495–500 (1995).
Mandel et al., "A Gene Triggering Flower Formation in Arabidopsis," *Nature* 377:522–524 (1995).
Kano–Murakami et al., "A Rice Homeotic Gene, OSH1, Causes Unusual Phenotypes in Transgenic Tobacco," *FEBS LETTERS* 334:365–368 (1993).
Hansen et al., "NTGLO: A Tobacco Homologue of the GLOBOSA Floral Homeotic Gene of *Antirrhinum majus*: cDNA Sequence and Expression Pattern," *Mol. Gen. Genet.* 239:310–312 (1993).
Ma et al., "AGL1–AGL6, an Arabidopsis Gene Family With Similarity to Floral Homeotic and Transcription Factor Genes," *Genes Dev.* 5:484–495 (1991).
Huijser et al., "Bracteomania, an Inflorescence Anomaly, is Caused by the Loss of Function of the MADS–Box Gene squamosa in *Antirrhinum majus*," *EMBO J.* 11:1239–1249 (1992).
Schwarz–Sommer et al., "Characterization of the Antirrhinum Floral Homeotic MADS–Box Gene deficiens: Evidence for DNA Binding and Autoregulation of its Persistent Expression Throughout Flower Development," *EMBO J.* 11:251–263 (1992).
Bradley et al., "Complementary Floral Homeotic Phenotypes Result From Opposite Orientations of a Transposon at the plena Locus of Antirrhinum," *Cell* 72:85–95 (1993).
Kempin et al., "Conversion of Perianth into Reproductive Organs by Ectopic Expression of the Tobacco Floral Homeotic Gene NAGI," *Plant Physiol.* 103:1041–1046 (1993).
Sommer et al., "Deficiens, a Homeotic Gene Involved in the Control of Flower Morphogenesis in *Antirrhinum majus*: The Protein Shows Homology to Transcription Factors," *EMBO J.* 9:605–613 (1990).
Angenent et al., "Differential Expression of Two MADS Box Genes in Wild–Type and Mutant Petunia Flowers," *Plant Cell* 4:983–993 (1992).

Chung et al., "Early Flowering and Reduced Apical Dominance Result form Ectopic Expression of a Rice MADS Box Gene," *Plant Mol. Biol.* 0:1–9 (1994). (Oct., vol. 26, No. 2, pp. 657–665).
Tsuchimoto et al., "Ectopic Expression of pMADS3 in Transgenic Petunia Phenocopies the Petunia blind Mutant," *Plant Cell* 5:843–853 (1993).
Coen et al., "floricaula: A Homeotic Gene Required for Flower Development in *Antirrhinum majus*,"0 *Cell* 63:1311–1322 (1990).
Trobner et al., "GLOBOSA: A Homeotic Gene Which Interacts With DEFICIENS in the Control of Antirrhinum Floral Organogenesis," *EMBO J.* 11:4693–4704 (1992).
Jack et al., "The Homeotic Gene APETALA3 of *Arabidopsis thaliana* Encodes a MADS Box and is Expressed in Petals and Stamens," *Cell* 68:683–697 (1992).
Tamas, "Hormonal Regulation of Apical Dominance." In: Davies PJ (ed), Plant Hormones and Their Role in Plant Growth and Development, pp. 393–410. Martinus Nijhoff Publ., Dordrecht, Netherlands (1987).
Schmidt et al., "Identification and Molecular Characterization of ZAG1, the Maize Homolog of the Arabidopsis Floral Homeotic Gene AGAMOUS," *Plant Cell* 5:729–737 (1993).
Pnueli et al., "Isolation of the Tomato AGAMOUS Gene TAG1 and Analysis of its Homeotic Role in Transgenic Plants," *Plant Cell* 6:163–173 (1994).
Weigel et al., "LEAFY Controls Floral Meristem Identity in Arabidopsis," *Cell* 69:843–859 (1992).
Mandel et al., "Molecular Characterization of the Arabidopsis Floral Homeotic Gene APETALA1," *Nature* 360:273–277 (1992).
Pnueli et al., "The MADS Box Gene Family in Tomato: Temporal EXpression During Floral Development, Conserved Secondary Structures and Homology with Homeotic Genes From Antirrhiunum and Arabidopsis," *Plant J.* 1:255–266 (1991).
Mandel et al., "Manipulation of Flower Structure in Transgenic Tobacco," *Cell* 71:133–143 (1992).

(List continued on next page.)

*Primary Examiner*—David T. Fox
*Attorney, Agent, or Firm*—Klarquist Sparkman Campbell Leigh & Whinston, LLP

[57] ABSTRACT

A rice cDNA clone termed OsMADS1 has been isolated. The sequence of this cDNA is presented. Expression of OsMADS1 in transgenic tobacco plants dramatically alters development, resulting in short, bushy, early flowering plants with reduced apical dominance. It is proposed that the OsMADS1 gene is involved in flower induction and may therefore be used to produce plants with altered phenotypic characteristics.

24 Claims, 10 Drawing Sheets

OTHER PUBLICATIONS

Gasser, "Molecular Studies on the Differentiation of Floral Organs," *Annu. Rev. Plant Physiol. Plant Mol. Biol. 42*:621–649 (1991).

Yanofsky et al., "The Protein Encoded by the Arabidopsis Homeotic Gene agamous Resembles Transcription Factors," *Nature 346*:35–39 (1990).

An, "Regulatory Genes Controlling Flowering Time or Floral Organ Development," *Plant Mol. Biol. 25*:335–337 (1994).

Coen, "The Role of Homeotic Genes in Flower Development and Evolution," *Annu. Rev. Plant Physiol. Plant Mol. Biol. 42*:241–279 (1991).

Pnueli et al., "The TM5 MADS Box Gene Mediates Organ Differentiation in Three Inner Whorls of Tomato Flowers," *Plant Cell 6*:175–186 (1994).

Mizukami et al., "Ectopic Expression of the Floral Homeotic Gene AGAMOUS in Transgenic Arabidopsis Plants Alters Floral Organ Identity," *Cell 71*:119–131 (1992).

```
  1 AAAACTAGCTTGCAAAGGGGATAGAGTAGTAGAGAGAGAGAGAGAGGAGAGGAGGAGGAA

61 GAAGATGGGGAGGGGGAAGGTGGAGCTGAAGCGGATCGAGAACAAGATCAGCCGGCAGGT
          MetGlyArgGlyLysValGluLeuLysArgIleGluAsnLysIleSerArgGlnVa   19
                                                                    MADS
121 GACGTTCGCCAAGCGCAGGAACGGCCTGCTCAAGAAGGCCTACGAGCTCTCCCTCCTCTG  -box
     lThrPheAlaLysArgArgAsnGlyLeuLeuLysLysAlaTyrGluLeuSerLeuLeuCy   39

181 CGACGCCGAGGTCGCCCTCATCATCTTCTCCGGCCGCGGCCGCCTCTTCGAGTTCTCCAG
     sAspAlaGluValAlaLeuIleIlePheSerGlyArgGlyArgLeuPheGluPheSerSe   59

241 CTCATCATGCATGTACAAAACCTTGGAGAGGTACCGCAGCTGCAACTACAACTCACAGGA
     rSerSerCysMetTyrLysThrLeuGluArgTyrArgSerCysAsnTyrAsnSerGlnAs   79

301 TGCAGCAGCTCCAGAAAACGAAATTAATTACCAAGAATACCTGAAGCTGAAAACAAGAGT
     pAlaAlaAlaProGluAsnGluIleAsnTyrGlnGluTyrLeuLysLeuLysThrArgVa   99

361 TGAATTTCTTCAAACCACACAGAGAAATATTCTTGGTGAGGATTTGGGCCCACTAAGCAT
     lGluPheLeuGlnThrThrGlnArgAsnIleLeuGlyGluAspLeuGlyProLeuSerMe  119
                                                                    K-box
421 GAAGGAGCTGGAGCAGCTTGAGAACCAGATAGAAGTATCCCTCAAACAAATCAGGTCAAG
     tLysGluLeuGluGlnLeuGluAsnGlnIleGluValSerLeuLysGlnIleArgSerAr  139

481 AAAGAACCAAGCACTGCTTGATCAGCTGTTTGATCTGAAGAGCAAGGAGCAACAGCTGCA
     gLysAsnGlnAlaLeuLeuAspGlnLeuPheAspLeuLysSerLysGluGlnGlnLeuGl  159

541 AGATCTCAACAAAGACTTGAGGAAAAAGTTACAGGAAACCAGTGCAGAGAATGTGCTCCA
     nAspLeuAsnLysAspLeuArgLysLysLeuGlnGluThrSerAlaGluAsnValLeuHi  179

601 TATGTCCTGGCAAGATGGTGGTGGGCACAGCGGTTCTAGCACTGTTCTTGCTGATCAGCC
     sMetSerTrpGlnAspGlyGlyGlyHisSerGlySerSerThrValLeuAlaAspGlnPr  199

661 TCATCACCATCAGGGTCTTCTCCACCCTCACCCAGATCAGGGTGACCATTCCCTGCAGAT
     oHisHisHisGlnGlyLeuLeuHisProHisProAspGlnGlyAspHisSerLeuGlnIl  219

721 TGGGTATCATCACCCTCATGCTCACCATCACCAGGCCTACATGGACCATCTGAGCAATGA
     eGlyTyrHisHisProHisAlaHisHisHisGlnAlaTyrMetAspHisLeuSerAsnGl  239

781 AGCAGCAGACATGGTTGCTCATCACCCCAATGAACACATCCCATCCGGCTGGATATGATG
     uAlaAlaAspMetValAlaHisHisProAsnGluHisIleProSerGlyTrpIle***    257

841 TGTGTGTTCAGTTCAGGCTTCAGGCTTCAGAGAAGCCAATGCAAACAGTGTCCTGTAATC

901 CAGTAATTACAGGGCATATGTAATGTAATGTAATGTAATCCCTGATCTATATTTTGCTAA

961 GTACGTGCGTGCTCTCTTACGACCTTCTCCCCCAAACAGTTAATCAGGGGAATAATAATT

1021 TCGTTTGATGCACGTACTGTATGTCTGTATCTGTCACTGTATCGTAGGACCGTCCATGTA

1081 TAACAATTTCCGTTTTGGATGTGGTAACAATTAATTGGCACTTAAATTTATATTTGTGAT

```
GRGKVELKRIENKISRQVTFAKRRNGLLKKAYELSLLCDAEVALIIFSGRGRLFEF  OsMADS1

****R*Q******N******S****A*******H*I*V********VV**HK*K***Y  Ap1
*****Q******N******S****G*******H****V********V**NK*K***Y  SQUA

****I*I*****TTN******C************V*****V****S*****Y**Y  AG
****I*I*****ITN******C*****************VV****S*****Y**Y  PLE

*G**R*Q****QTN**YS***F*HTV***R*SI*M**SSNK*H*Y  Ap3
A***IQI******QTN******YS*******F****H****V****K*SI*MI*STQK*H*Y  DEF A
```

FIG. 1B

GENE CONTROLLING FLORAL DEVELOPMENT AND APICAL DOMINANCE IN PLANTS

BACKGROUND OF THE INVENTION

Rapid progress has been made towards elucidating the underlying mechanisms controlling flower development in distantly related dicot plant species [5, 8]. These studies led to the isolation of a family of genes which encode regulatory proteins. These include AGAMOUS (AG) [30], APETALA1 (AP1) [15], and APETALA3 (AP3) [11] in *Arabidopsis thaliana*, and DEFICIENS A (DEFA) [25], GLOBOSA (GLO) [27], SQUAMOSA (SQUA) [10], and PLENA (PLE) [4] in *Antirrhinum majus*. Mutations in an AG or PLE gene resulted in homeotic alterations of stamen and carpel. Genetic studies have shown that DEFA, GLO and AP3 genes are essential for petal and stamen development. AP1 and SOUA genes which are expressed in young flower primordia are necessary for transition of an inflorescence meristem into a floral meristem. Sequence analysis of these genes revealed that the gene products contain a conserved MADS box region [4, 10, 11, 15, 25, 27, 30] which is probably a DNA-binding domain [24]. Using these clones as probes, MADS box genes have also been isolated from other species including tomato [17], tobacco [12], petunia [2], *Brassica napus* [14], and maize [23].

Transgenic approaches were undertaken to study the functional roles of the MADS box genes. Genetic complementation of the ag-2 mutant by the AG gene demonstrated that the gene product is involved in stamen and carpel development [30]. Ectopic expression of the AG genes from *A. thaliana, B. napus*, petunia, tobacco, and tomato resulted in homeotic conversion of sepal to carpel and petal to stamen, mirroring the ap2 mutant phenotype [12, 14, 16, 19, 28]. These results support the hypothesis that AG and AP2 act in an antagonistic fashion. Antisense approaches were also used to reveal the functional role of the tomato MADS box genes [18, 19]. Transgenic plants that express tomato AG antisense RNA displayed the ag mutant phenotypes. Antisense expression of the tomato TM5 MADS box gene resulted in morphological changes in the three inner whorls of transgenic plants.

SUMMARY OF THE INVENTION

In this application we disclose a MADS-box homologue from rice, OsMADS1 (SEQ ID NO:1) and the effects of its expression in tobacco plants.

According to one aspect of the present invention, isolated polynucleotides are provided that comprise at least 30 consecutive nucleotides of OsMADS1 sequence (SEQ ID NO:1). Also provided are isolated polynucleotide sequences that hybridize to the OsMADS1 gene (SEQ ID NO:1) under stringent conditions.

According to another aspect of the present invention, the following are also provided, for example: probes, vectors, cells, and transgenic plants that comprise such polynucleotides.

According to another aspect of the present invention, related methods are provided for making transgenic plants.

According to yet another aspect of the present invention, purified proteins are provided that comprise least part of the OsMADS1 amino acid sequence (SEQ ID NO:1) e.g., amino acids 2 to 57.

BRIEF DESCRIPTION OF THE DRAWINGS

FIGS. 1A–1B show nucleotide and deduced amino acid sequences of OsMADS1 cDNA (FIG. 1A), and comparison of MADS box regions with other MADS box proteins (FIG. 1B).

DETAILED DESCRIPTION OF THE PREFERRED EMBODIMENTS

Materials and Methods

Figures 2A, 2B:
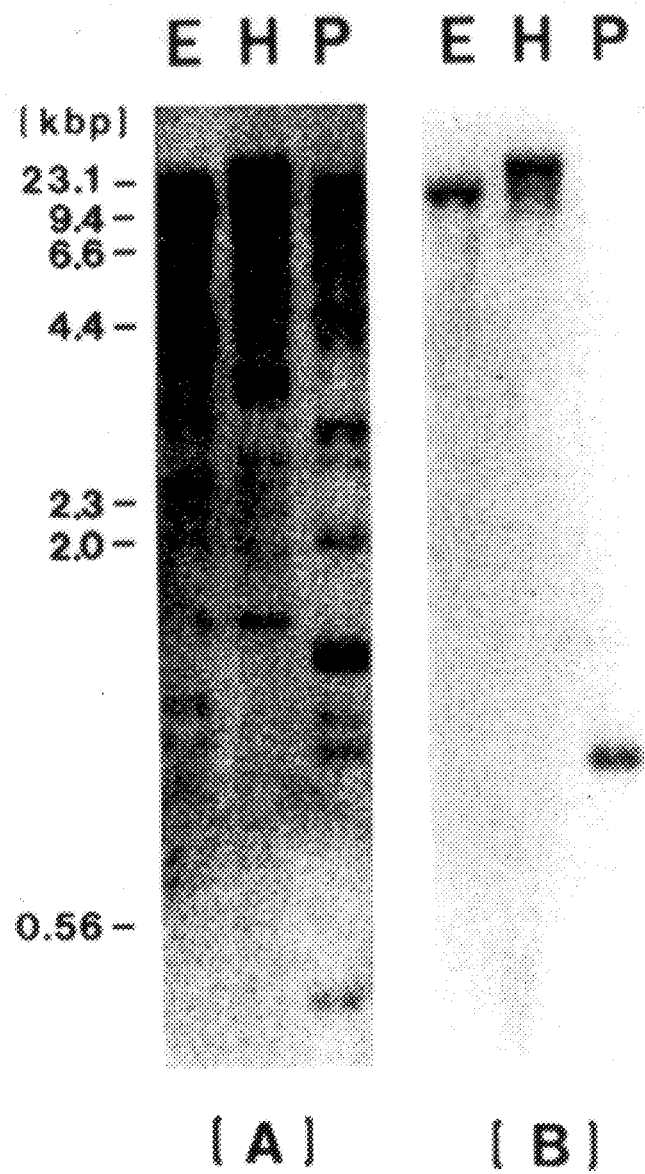
FIG. 2 shows Southern blot analysis of rice DNA probed with the OsMADS1 cDNA.

Bacterial strains, plant materials, and plant transformation.

*Escherichia coli* MC1000 (ara, leu, lac, gal, str) was used as the recipient for routine cloning experiments. *Agrobacterium tumefaciens* LBA4404 [9] containing the Ach5 chromosomal background and a disarmed helper-Ti plasmid pAL4404, was used for transformation of tobacco plants (Nicotiana tabacum L. cv. Petit Havana SR1) by the cocultivation method [1]. Transgenic plants were maintained in greenhouse conditions. Rice (*Oryza sativa* L. cv. M201) plants were grown in a growth chamber at 26° C. with 10.5 h day cycle.

cDNA library construction and molecular characterization.

A cDNA library was constructed using the λ ZapII vector (Stratagene) and poly(A)$^+$mRNA isolated from rice flower. An adapter containing Eco RI and Not I sites (Pharmacia Biotech) was used to ligate the vector and cDNA. The library was divided into 20 sublibraries and amplified in an *E. coli* host strain, XL-1 Blue [F'::Tn10 proA$^+$B$^+$, lacIq, (lacZ,)M15/recA1. endA1, gyrA96 (Nar') thi, hsdR17(rk$^-$, mk$^+$), sup44, relA1, lac] (Stratagene). Plaque hybridization was performed with 10$^5$ plaques which were lifted onto nitrocellulose membranes. The plasmid pBluescript containing the OsMADS cDNA was in vivo rescued from the bacteriophage λ using fl helper phage, R408 (Stratagene). Both strands of the cDNA inserts were sequenced by the dideoxynucleotide chain termination method using double-stranded DNA as a template [22].

Southern and northern analyses

Genomic DNA was prepared from two-week-old rice seedlings by the CTAB (cetyltrimethylammonium bromide) method [20]. Four μg of DNA was digested with appropriate restriction enzymes, separated on a 0.7% agarose gel, blotted onto a nylon membrane, and hybridized with a $^{32}$P-labeled probe by the random priming method [21]. Ten μg of total RNAs isolated by the guanidium thiocyanate method were used for the northern analysis [21].

In situ localization

Rice flowers were dehydrated with ethanol, fixed (1.4% glutaraldehyde, 2% paraformaldehyde, 50 mM PIPES, pH 7.2), and embedded in paraffin. Eight-μm sections were attached to gelatin-coated glass slides and hybridized with $^{35}$S-labeled antisense RNA [7]. The RNA probe was prepared by in vitro transcription using the pBluscript carrying OsMADS 1 cDNA clone as a template. The sections were coated with an X-ray emulsion film and exposed for four days. The samples were stained with 0.5% toluidine blue to visualize tissue sections. Photographs were taken with a bright field microscope.

Results

Isolation of a rice cDNA clone encoding MADS box protein

We have isolated a cDNA clone, OsMADS1, by screening a λ ZapII cDNA library prepared from immature rice flower mRNA using mixed probes of different MADS box cDNA clones isolated from Arabidopsis [13, 30], Brassica [14], tobacco [12], and tomato [17]. DNA sequence analysis showed that the rice clone encodes a putative protein of 257 amino acid residues (FIG. 1A; SEQ ID NO.1). The deduced amino acid sequence contains the conserved MADS box domain between the amino acids 2 and 57 (FIG. 1B; SQE ID NOS.2–8). A second domain, called the K box, present in the MADS box proteins is located between the residues 90 and 143. These observations suggest that OsMADS1 is a member of the MADS box gene family. Among characterized MADS box proteins, the OsMADS1 amino acid sequence is most homologous to AP1 (44.4% identity) and SQUA (42.6% identity). In addition, OsMADS1 shows extensive similarity to the functionally anonymous Arabidopsis MADS box genes, AGL2 (56.2% identity) and AGL4 (55.4% identity).

Southern blot analysis

To determine the number of MADS box genes present in rice, DNA gel blot analysis was performed. FIG. 2 shows that more than ten restriction fragments hybridized with the entire cDNA probe whereas a single fragment was detected by a probe lacking the conserved MADS box region. This result indicates that the rice genome contains a high number of genes encoding MADS box proteins, similar to other plant species [2, 13, 17, 23].

Expression pattern of OsMADS1

Figures 3A, 3B:
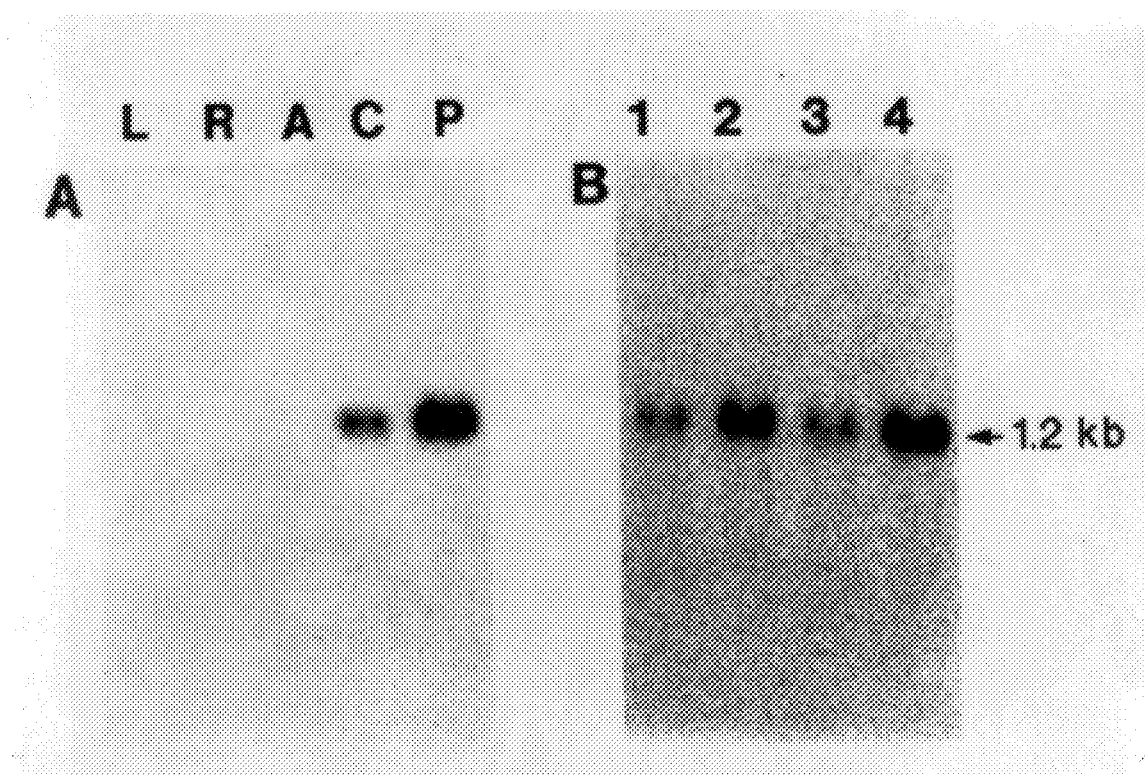
FIG. 3 shows Northern blot analysis of OsMADS1 transcript in rice in various organs(A), and the temporal expression pattern during flower development (B).
Figure 4A:
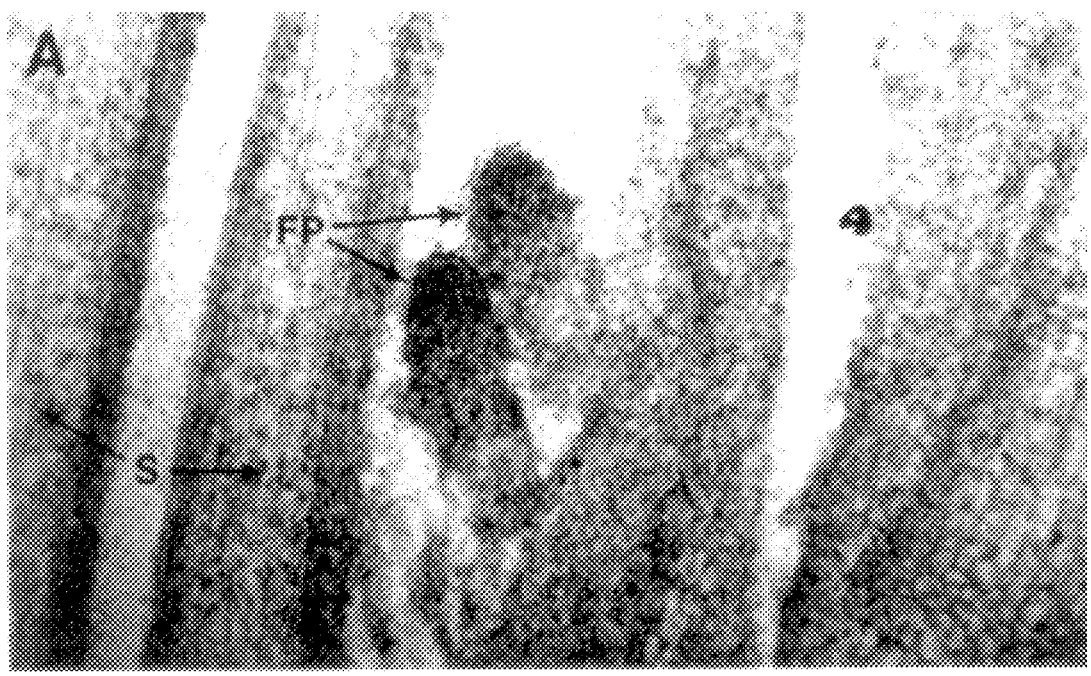
FIG. 4 shows localization of the OsMADS1 transcript in rice flower and phenotypes of transgenic tobacco plants expressing OsMADS1.
Figure 4B:
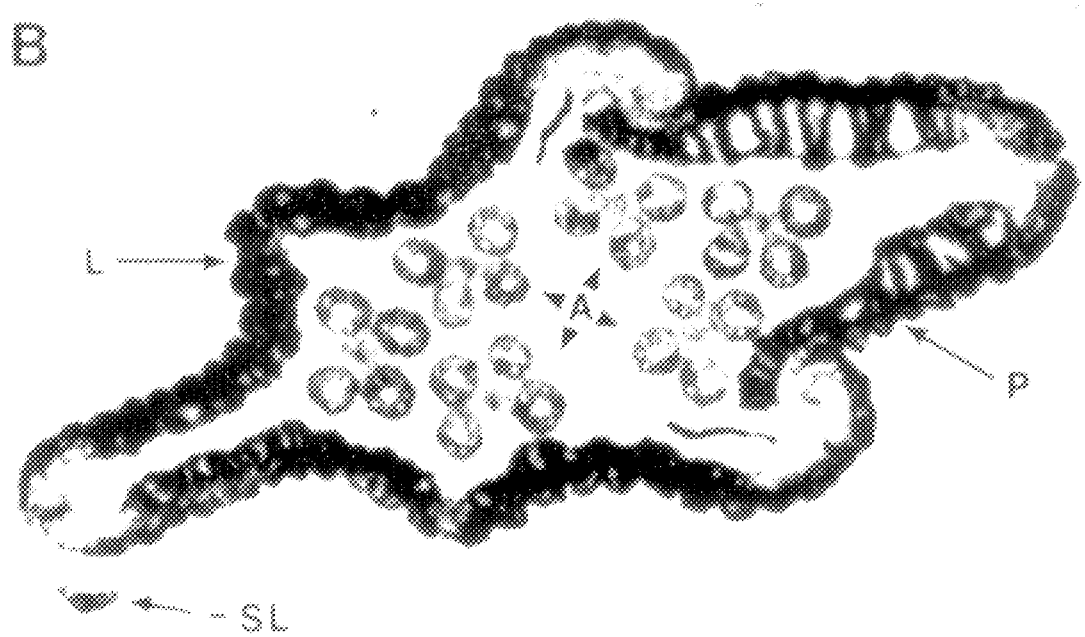
Figure 4C:
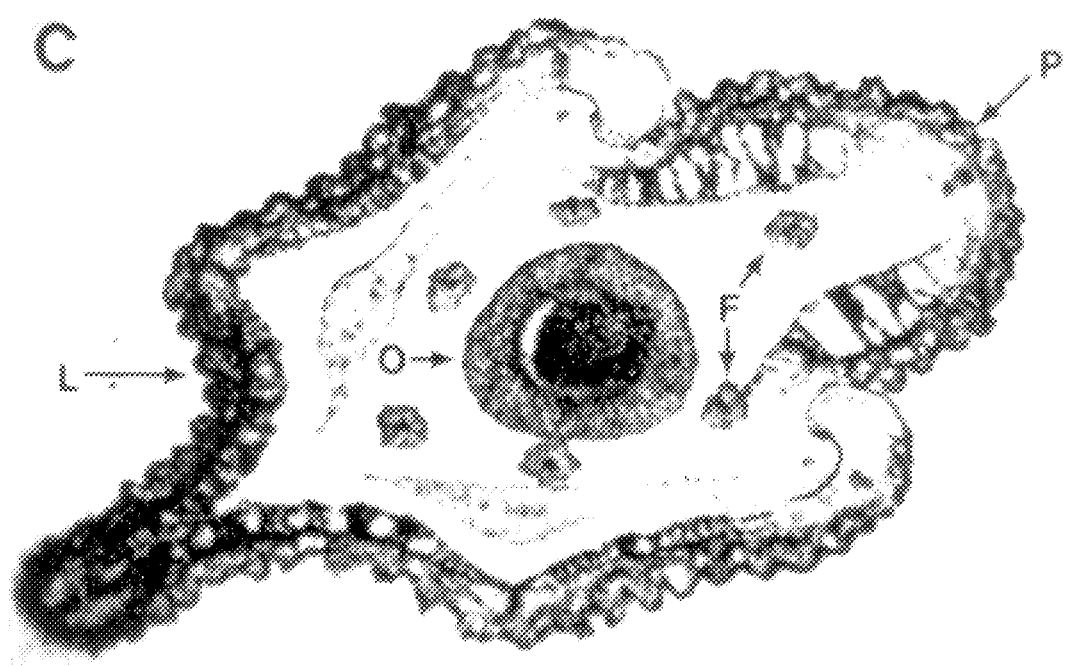

Northern blot analyses were conducted to study the expression pattern of the OsMADS 1 gene (FIG. 3). RNA samples were hybridized with the probe lacking the conserved MADS box region to avoid cross hybridization and obtain specific expression pattern of the gene. The OsMADS1 transcripts were present in palea, lemma, and carpel, but not in anther or vegetative organs (FIG. 3A). The gene was active during young inflorescence stage and the expression continued into the early and late vacuolated pollen stage (FIG. 3B). In situ experiments revealed that the OsMADS1 transcript was uniformly present in young flower prinmordia during early flower development and later became localized in certain floral organs (FIG. 4A–4C). In young inflorescence, strong hybridization signals were detected in flower primordia but not in other tissues. In vacuolated pollen-stage flower, OsMADS1 RNA was detected in palea, lemma, and ovary. However, hybridization signal was not uniform in these tissues. In particular, the tissues near the palea/lemma junction and the palea tissues covered by lemma exhibited little or no expression of the gene. No significant signal was observed from anther, filament, or sterile lemma These results indicate that the OsMADS1 gene is preferentially expressed in certain floral tissues as has been observed with most MADS box genes.

Ectopic expression of OsMADS1

Figure 4D:
Figure 4E:

It was shown previously that ectopic expression of the floral homeotic gene alters floral organ identity in homologous [12, 16, 19, 28] and heterologous systems [14]. In order to characterize the functional role of OsMADS1, we have used tobacco plants as a heterologous expression system. The cDNA clone encoding the entire OsMADS1 coding region was placed under the control of cauliflower mosaic virus 35S promoter [3] and transcript 7 terminator using a binary vector pGA748, which is a derivative of pGA643 [1]. The chimeric molecule (pGA1209) was transferred to tobacco (Nicotiana tabacum cv. Petite Havana SR1) plants using the Agrobacterium-mediated Ti plasmid vector system [1]. Twenty independent transgenic plants were studied to avoid any artifact. Results showed that most of the primary transgenic plants flowered much earlier compared to the control plants which were transformed with the Ti plasmid vector alone. These plants were significantly shorter and contained several lateral branches (FIG. 4D–4E). These phenotypes were inherited to the next generation as a dominant Mendelian trait. Northern blot analysis was conducted on seven transgenic plants which displayed the early flowering phenotype. The results (FIG. 5) showed that all of the plants accumulated the OsMADS1 transcripts in both vegetative and reproductive organs. Although there were significant differences in gene expression among transgenic plants, the relative expression level was similar between the leaf and flower. Transgenic plant #7, which displayed the most severe symptoms, accumulated the highest level of the transcript. Plants #4, #5, #6, with less severely altered phenotypes, expressed the gene at reduced levels, indicating that the level of OsMADS1 RNA correlated with phenotype. However, progeny from the same parent displayed phenotypic variation. The basis of this variation was investigated with T1 offspring of the transgenic plant #2 in which the transgene segregates as a single locus. OsMADS1 homozygotes were much shorter (34.2±0.8 cm) compared to heterozygotes (51.6±1.4 cm), while the wild-type tobacco plants were 119.8±2.2 cm. The homozygotes flowered two days earlier than the heterozygotes and eight days earlier than the wild type. This indicates that the variation was due to the gene dosage. Table 1 summarizes characteristics of four independently transformed plants from the T1 generation. Transgenic plants flowered 7 to 10 days earlier than wild-type and their height and internode length appear to be significantly reduced.

Discussion

We report here the isolation and characterization of a rice MADS box gene The deduced amino acid sequence of the rice gene showed a high homology to MADS box proteins, especially in the MADS box domain. The OsMADS1 clone appears to be nearly full length since the estimated transcript length by northern analysis is similar to that of the cDNA clone. The conserved MADS box region is located immediately after the start methionine codon in the rice gene as has been observed in most MADS box genes. Therefore, it is unlikely that the rice clone encodes for a truncated protein. The OsMADS1 sequence is most similar to AGL2, AGL4, AP1 and SQUA. The OsMADS1 gene is initially expressed uniformly in young flower primordia and in later developmental stages becomes localized in palea, lemma, and ovary. Vegetative tissues do not show any expression of the gene. The expression pattern of the OsMADS1 gene closely resembled that of AP1 and SQUA [10, 15]. Flower specific expression is also common for other MADS box genes [2, 11, 12, 13, 15, 17, 23, 25, 28]. Southern analysis revealed that there are at least 10 genes which share a significant homology with the OsMADS1. We have isolated nine independent cDNA clones which contain the conserved MADS box. Detailed characterization of these clones will be reported in a future publication.

We have studied the role of the rice MADS box gene by expressing it in tobacco plants. Ectopic expression of the rice OsMADS1 resulted in early flowering and dwarf phenotypes. It is possible that the rice OsMADS1 product may induce expression of genes which are involved in the induction of flowering. Ectopic expression of OsMADS1 results in accumulation of a protein which may act as a positive regulatory factor similar to AP1 or SQUA. Since the 35S promoter is active in most cell types, the OsMADS1 protein is likely accumulated in shoot meristem and inflorescence meristem where the AP1 (SQUA)-like gene is not activated yet. It was reported earlier that at least two genes, AP1 and LEAFY, are required for the transition of inflorescence meristem into floral meristem in Arabidopsis [29]. Similarly, SQUA and FLORICAULA are required for floral organ induction in *Antirrhinum majus* [6]. It was determined that AP1 and SQUA belong to the MADS box gene family [6, 29]. If AP1 is normally expressed later than LEAFY, the ectopic expression of OsMADS1 may bypass the transient period required for normal floral organ development. Alternatively, the protein may interact with a negative factor which normally inhibits flowering. It is also possible that a higher expression of OsMADS1 may enhance the response to flower promoting signals.

Although the exact mechanism by which the gene exerts its effects is not known, we have demonstrated that the OsMADS1 is potentially useful for shortening flowering time and for reducing apical dominance in certain plant species. There is no previous report that other MADS box genes have been used for induction of early flowering and dwarfing. These interesting phenotypes were not apparent in their juvenile state. However, in transgenic plants the axillary bud growth was initiated during the early stage of floral meristem development. The growing shoot apex is known to exert an influence over a range of developmental events including axillary bud growth [26]. The effect is most highly observed early in plant development. As plants mature, the emergence of floral organs releases inhibition of the lateral buds and allows them to develop. The active substance responsible for the apical dominance in several plant species has been identified to be a plant growth factor, indoleacetic acid. In the transgenic OsMADS1 plants, the dwarf phenotype may be the result of altered hormonal status due to early flowering.

Early flowering and dwarf phenotypes are important agronomic traits since a balance between vegetative and reproductive growth is a crucial factor that controls crop yields. Enhancement of harvest index in grain crops has been accomplished by the use of dwarfing genes. However, isolation of these genes has been difficult. Moderated expression of the OsMADS1 gene by means of tissue-specific promoters may make it useful as an alternative source of early flowering and dwarfing gene to increase crop productivity.

DEFINITIONS

In order to facilitate review of the various embodiments of the invention and an understanding of various embodiments and constituents used in making the invention, the following definition of terms is provided:

DNA: deoxyribonucleic acid. DNA is a long chain polymer which comprises the genetic material of most living organisms (some viruses have genes comprising ribonucleic acid [RNA]). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed. The nomenclature for DNA bases as set forth at 37 CFR § 1.822 is used.

cDNA (complementary DNA): a piece of DNA lacking internal, non-coding segments (introns) and regulatory sequences which determine transcription. cDNA is synthesized in the laboratory by reverse transcription from messenger RNA extracted from cells.

OsMADS1 gene: a rice gene associated with flower induction and altered developmental phenotypes, as described in greater detail above. This definition is understood to include the various sequence polymorphisms that exist, wherein nucleotide substitutions in the gene sequence do not affect the essential functions of the gene product. This term relates primarily to an isolated coding sequence, but can also include some or all of the flanking regulatory elements and/or intron sequences.

OsMADS1 protein: the protein encoded by the OsMADS1 gene. This definition is understood to include the various sequence polymorphisms that exist, wherein amino acid substitutions in the protein sequence do not affect the essential functions of the protein.

Isolated: requires that the material be removed from its original environment. For example, a naturally occurring DNA molecule present in a living animal is not isolated, but the same DNA molecule, separated from some or all of the coexisting materials in the natural system, is isolated.

ORF: open reading frame. Contains a series of nucleotide triplets (codons) coding for amino acids without any termination codons. These sequences are usually translatable into protein.

PCR: polymerase chain reaction. Describes a technique in which cycles of denaturation, annealing with primer, and then extension with DNA polymerase are used to amplify the number of copies of a target DNA sequence.

Protein: a biological molecule expressed by a gene and comprised of amino acids. The standard three-letter nomenclature (as set forth at 37 C.F.R. § 1.822) is used to identify the amino acids.

Purified: the term "purified" does not require absolute purity; rather, it is intended as a relative definition. Thus, for example, a purified protein preparation is one in which the specific protein referred to is more pure than the protein in its natural environment within a cell.

Additional definitions of common terms in molecular biology may be found in Lewin, B. "Genes IV" published by Oxford University Press.

Preferred Method of Making cDNA Clones

Based upon the availability of the OsMADS1 cDNA and the nucleotide sequence thereof, as disclosed above, other rice MADS1 genes (e.g., alleles of OsMADS1) or other nucleotide sequences having sufficient sequence similarity may be readily obtained by cloning methods known in the art. For example, the polymerase chain reaction (PCR) may be utilized in conjunction with oligonucleotide primers derived from the presented DNA sequence to obtain such similar nucleotide sequences. Variations in amplification conditions may be required to accommodate primers of differing lengths; such considerations are well known in the art and are discussed in Innis et al. (1990).

Cloning of the OsMADS1 Genomic Gene and Characterization of the Exon Structure of this Gene.

Following transcription of a gene containing introns, the intron sequences are removed from the RNA molecule in a process termed splicing prior to translation of the RNA molecule which results in production of the encoded protein. When the RNA molecule is spliced to remove the introns, the cellular enzymes that perform the splicing function recognize sequences around the intron/exon border and in this manner recognize the appropriate splice sites.

The provision herein of the OsMADS1 cDNA sequence enables the cloning of the entire OsMADS1 gene (including the promoter and other regulatory regions and the intron sequences) and the determination of its nucleotide sequence. Having provided a genomic clone for the OsMADS1 gene, it will be apparent to one skilled in the art that either the genomic clone or the cDNA or sequences derived from these clones may be utilized in applications of this invention, including but not limited to, studies of the expression of the OsMADS1 gene, studies of the function of the OsMADS1 protein, and the generation of antibodies to the OsMADS1 protein. Descriptions of applications describing the use of OsMADS1 cDNA are therefore intended to comprehend the use of the genomic OsMADS1 gene.

Nucleotide Sequence Variants of OsMADS1 cDNA and Amino Acid Sequence Variants of OsMADS1 Protein Having presented the nucleotide and, the amino acid sequence of the OsMADS1 protein, this invention now also facilitates the creation of DNA molecules, and thereby proteins, which are derived from those disclosed but which vary in their precise nucleotide or amino acid sequence from those disclosed. Such variants may be obtained through a combination of standard molecular biology laboratory techniques and the nucleotide sequence information disclosed by this invention.

Variant DNA molecules include those created by standard DNA mutagenesis techniques, for example, M13 primer mutagenesis. Details of these techniques are provided in Sambrook et al. (1989), Ch. 15. By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristic of the OsMADS1 protein are comprehended by this invention. Also within the scope of this invention are small DNA molecules which are derived from the disclosed DNA molecules. Such small DNA molecules include oligonucleotides suitable for use as hybridization probes or polymerase chain reaction (PCR) primers. As such, these small DNA molecules will comprise at least a segment of an OsMADS1 cDNA molecule or the OsMADS1 genomic DNA and, for the purposes of PCR, will comprise at least a 10–15 nucleotide sequence and, more preferably, a 15–30 nucleotide sequence of the OsMADS1 cDNA or the OsMADS1 gene. DNA molecules and nucleotide sequences which are derived from the disclosed DNA molecules as described above may also be defined as DNA sequences which hybridize under stringent conditions to the DNA sequences disclosed, or fragments thereof.

Hybridization conditions resulting in particular degrees of stringency will vary depending upon the nature of the hybridization method of choice and the composition and length of the hybridizing DNA used. Generally, the temperature of hybridization and the ionic strength (especially the Na$^+$ concentration) of the hybridization buffer will determine the stringency of hybridization. Calculations regarding hybridization conditions required for attaining particular degrees of stringency are discussed by Sambrook et al. (1989), chapters 9 and 11, herein incorporated by reference. By way of illustration only, a hybridization experiment may be performed by hybridization of a DNA probe (for example, a deviation of the OsMADS1 cDNA) to a target DNA molecule which has been electrophoresed in an agarose gel and transferred to a nitrocellulose membrane by Southern blotting (Southern, 1975), a technique well known in the art and described in (Sambrook et al., 1989). Hybridization with a target probe labeled with [$^{32}$P]-dCTP is generally carried out in a solution of high ionic strength such as 6×SSC at a temperature that is 20°–25° C. below the melting temperature, $T_m$, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to 10$^9$ CPM/μg or greater). Following hybridization, the nitrocellulose filter is washed to remove background hybridization. The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton and McCarthy, 1962):

$$T_m = 81.5° C. - 16.6(\log_{10}[Na^+]) + 0.41(\%G+C) - 0.63(\% formamide) - (600/l)$$

Where l=the length of the hybrid in base pairs. This equation is valid for concentrations of Na$^+$ in the range of 0.01M to 0.4M, and it is less accurate for calculations of $T_m$ in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al., 1989).

The $T_m$ of double-stranded DNA decreases by 1°–1.5° C. with every 1% decrease in homology (Bonner et al., 1973). Therefore, for this given example, washing the filter in 0.3×SSC at 59.4°–64.4° C. will produce a stringency of hybridization equivalent to 90%; that is, DNA molecules with more than 10% sequence variation relative to the probe molecule will not hybridize. Alternatively, washing the hybridized filter in 0.3×SSC at a temperature of 65.4°–68.4° C. will yield a hybridization stringency of 94%; that is, DNA molecules with more than 6% sequence variation relative to the probe molecule will not hybridize. The above example is given entirely by way of theoretical illustration. One skilled in the art will appreciate that other hybridization techniques may be utilized and that variations in experimental conditions will necessitate alternative calculations for stringency.

In preferred embodiments of the present invention, stringent conditions may be defined as those under which DNA molecules with more than 25% sequence variation (also termed "mismatch") will not hybridize. In a more preferred embodiment, stringent conditions are those under which DNA molecules with more than 15% mismatch will not hybridize, and more preferably still, stringent conditions are those under which DNA sequences with more than 10% mismatch will not hybridize. In a most preferred embodiment, stringent conditions are those under which DNA sequences with more than 6% mismatch will not hybridize.

The degeneracy of the genetic code further widens the scope of the present invention as it enables major variations in the nucleotide sequence of a DNA molecule while maintaining the amino acid sequence of the encoded protein. The genetic code and variations in nucleotide codons for particular amino acids is presented in Tables 2-A and 2-B. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein also comprehended by this invention.

TABLE 2-A

The Genetic Code

| First Position (5' end) | Second Position | | | Third Position (3' end) |
|---|---|---|---|---|
| | T | C | A | G |
| T | Phe | Ser | Tyr | Cys | T |
| | Phe | Ser | Tyr | Cys | C |
| | Leu | Ser | Stop (och) | Stop | A |
| | Leu | Ser | Stop (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Asn | Ser | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

"Stop (och)" stands for the ocre termination triplet, and "Stop (amb)" for the amber. ATG is the most common initiator codon; GTG usually codes for valine, but it can also code for methionine to initiate an mRNA chain.

TABLE 2-B

The Degeneracy of the Genetic Code

| Number of Synonymous Codons | Amino Acid | Total Number of Codons |
|---|---|---|
| 6 | Leu, Ser, Arg | 18 |
| 4 | Gly, Pro, Ala, Val, Thr | 20 |
| 3 | Ile | 3 |
| 2 | Phe, Tyr, Cys, His, Gln, Glu, Asn, Asp, Lys | 18 |
| 1 | Met, Trp | 2 |
| Total number of codons for amino acids | | 61 |
| Number of codons for termination | | 3 |
| Total number of codons in genetic code | | 64 |

One skilled in the art will recognize that the DNA mutagenesis techniques described above may be used not only to produce variant DNA molecules, but will also facilitate the production of proteins which differ in certain structural aspects from the OsMADS1 protein, yet which proteins are clearly derivative of this protein and which maintain the essential characteristics of the OsMADS1 protein. Newly derived proteins may also be selected in order to obtain variations on the characteristic of the OsMADS1 protein, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure (EP 75,444A).

Substitutional variants are those in which at least one residue in the amino acid sequence has been removed and a different residue inserted in its place. Such substitutions generally are made in accordance with the following Table 3 when it is desired to finely modulate the characteristics of the protein. Table 3 shows amino acids which may be substituted for an original amino acid in a protein and which are regarded as conservative substitutions.

TABLE 3

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function are made by selecting substitutions that are less conservative than those in Table 3, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The OsMADS1 gene, OsMADS1 cDNA, DNA molecules derived therefrom and the protein encoded by the cDNA and derivative DNA molecules may be utilized in aspects of both the study of the structure and function of the OsMADS1 protein, for altering the flowering and development of transgenic plants expressing the OsMADS1 protein. Those skilled in the art will recognize that the utilities herein described are not limited to the specific experimental modes and materials presented and will appreciate the wider potential utility of this invention.

Expression of OsMADS1 cDNA Sequences

With the provision of the OsMADS1 cDNA, the expression and purification of the OsMADS1 protein by standard laboratory techniques is now enabled. The purified protein may be used for the production of specific antibodies useful in cloning genes encoding proteins having amino acid sequence homology and thus sharing antigenic determinants with OsMADS1, and for studies of the structure and function of the OsMADS1 protein. Furthermore, the sequence of the OsMADS1 cDNA can be used to better understand the expression of the OsMADS1 gene and the function of its product, leading to a better understanding of and a greater ability to manipulate plant development and flowering.

Partial or full-length cDNA sequences which encode the subject protein may be ligated into bacterial expression vectors. Methods for expressing large amounts of protein from a cloned gene introduced into *Escherichia coil* (*E. coli*) may be utilized for the purification, localization and functional analysis of proteins. For example, fusion proteins consisting of amino terminal peptides encoded by a portion of the *E. coli* lacZ or trpE gene linked to OsMADS1 proteins may be used to prepare polyclonal and monoclonal antibodies against these proteins by methods well known in the art. Thereafter, these antibodies may be used to purify proteins by immunoaffinity chromatography, in diagnostic assays to quantitate the levels of protein and to localize proteins in tissues and individual cells by immunofluorescence.

Intact native protein may also be produced in *E. coil* in large amounts for functional studies. Methods and plasmid vectors for producing fusion proteins and intact native proteins in bacteria are described in Sambrook et al. (1989) (ch. 17, herein incorporated by reference). Such fusion proteins may be made in large amounts, are easy to purify, and can be used to elicit antibody response. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (1989) and are well known in the art. If the protein, when expressed at high levels, is found in insoluble inclusion bodies, the protein may be extracted from the inclusion bodies as described by Sambrook et al. (1989) (ch. 17).

Vector systems suitable for the expression of lacZ fusion genes include the pUR series of vectors (Ruther and Muller-Hill, 1983), pEX1-3 (Stanley and Luzio, 1984) and PMR100 (Gray et al., 1982). Vectors suitable for the production of intact native proteins include pKC30 (Shimatake and Rosenberg, 1981), pKK177-3 (Amann and Brosius, 1985) and pET-3 (Studiar and Moffatt, 1986). OsMADS1 fusion proteins may be isolated from protein gels, lyophilized, ground into a powder and used as an antigen.

The OsMADS1 DNA sequence can also be transferred to other cloning vehicles, such as other plasmids, bacteriophages, cosmids, animal viruses and yeast artificial chromosomes (YACs) (Burke et al., 1987). These vectors may then be introduced into a variety of hosts including somatic cells, and simple or complex organisms, such as bacteria, fungi (Timberlake and Marshall, 1989), invertebrates, plants (Gasser and Fraley, 1989), and pigs (Pursel et al., 1989), which cell or organisms are rendered transgenic by the introduction of the heterologous OsMADS1 cDNA.

Production of an Antibody to OsMADS1 Protein

Monoclonal or polyclonal antibodies may be produced to either the normal OsMADS1 protein or mutated forms of this protein. The determination that an antibody specifically detects the OsMADS1 protein is made by any one of a number of standard immunoassay methods; for instance, the Western blotting technique (Sambrook et al., 1989). To determine that a given antibody preparation (such as one produced in a mouse) specifically detects the OsMADS1 protein by Western blotting, total cellular protein is extracted from rice cells and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the OsMADS1 protein will, by this technique, be shown to bind to the OsMADS1 protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-OsMADS1 protein binding.

Substantially pure OsMADS1 protein suitable for use as an immunogen is isolated from rice cells or other cells in which it is produced, as described. Concentration of protein in the final preparation is adjusted, for example, by concentration on an Amicon filter device, to the level of a few micrograms per milliliter. Monoclonal or polyclonal antibody to the protein can then be prepared as follows:

Monoclonal Antibody Production by Hybridoma Fusion. Monoclonal antibody to epitopes of the OsMADS1 protein identified and isolated as described can be prepared from murine hybridomas according to the classical method of Kohler and Milstein (1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980), and derivative methods thereof. Selected positive clones can be expanded and their monoclonal antibody product harvested for use. Detailed procedures for monoclonal antibody production are described in Harlow and Lane (1988).

Polyclonal Antibody Production by Immunization. Polyclonal antiserum containing antibodies to heterogenous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher (1980).

Antibodies Raised against Synthetic Peptides. A third approach to raising antibodies against the OsMADS1 protein is to use synthetic peptides synthesized on a commercially available peptide synthesizer based upon the predicted amino acid sequence of the OsMADS1 protein.

Antibodies Raised by Injection of OsMADS1 Gene. Antibodies may be raised against the OsMADS1 protein by subcutaneous injection of a DNA vector which expresses the OsMADS1 protein into laboratory animals, such as mice. Delivery of the recombinant vector into the animals may be achieved using a hand-held form of the Biolistic system (Sanford et al., 1987) as described by Tang et al. (1992).

Antibody preparations prepared according to these protocols are useful in quantitative immunoassays which determine concentrations of antigen-bearing substances in biological samples; they are also used semi-quantitatively or qualitatively to identify the presence of antigen in a biological sample.

Cloning and Analysis of the OsMADS1 Genomic Gene

The genomic gene from which the OsMADS1 cDNA was derived may now be cloned from a rice genomic library using regions of the disclosed OsMADS1 cDNA as probes to protect hybridizing clones. Rice genomic libraries which are screened for these clones may be purchased commerically or may be constructed in the laboratory by methods well known in the art.

The methodology described for cloning the rice genomic OsMADS1 gene described may be followed for the cloning of the gene from other plants. Methods for labelling fragments of the OsMADS1 cDNA for use as a probe and for screening such libraries are widely known, and the detailed methodologies are presented in Sambrook et al. (1989). Following the isolation of hybridizing genomic DNA clones, the clones are analyzed by methods including restriction mapping and DNA sequence analysis to determine the extent of the genomic OsMADS1 gene. The complete gene may need to be assembled from several individual clones if it is of large size. Additional internal or terminal sequences not present in the assembled gene may be obtained by reprobing the library using probes derived from regions adjacent to the missing sequences. Alternatively, polymerase chain reaction (PCR) based methods such as inverse PCR and ligation mediated PCR may be used to amplify and clone the missing sequences from total rice DNA. The identification and characterization of regulatory elements flanking the OsMADS1 genomic gene may be accomplished by methods well known in the art.

Cross-Species Hybridization

A cross-species Southern blot hybridization experiment is performed to determine whether homologs of the OsMADS1 gene are conserved across species. The OsMADS1 cDNA is used as a probe. The labelled fragment is hybridized under low stringency conditions to a Southern blot prepared from DNA from multiple species digested using one or a number of different restriction enzymes using standard procedures (Sambrook et al., 1989). The autoradiograph is exposed for the requisite time with an intensifying screen (Dupont, Wilmington, Del.).

Cloning of OsMADS1 homologs from other species enables the identification of regions of sequence conservation indicative of function, which are presently difficult to define with the limited data available.

Practicing the present invention requires the manipulation of DNA sequences, including the OsMADS1 and rice MADS box sequences, using molecular biological techniques. DNA sequences can be manipulated with standard procedures known in the art, such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR. Details of these techniques are provided in standard laboratory manuals such as Sambrook et al. (1989) and Ausubel et al. (1992).

Practicing the invention also requires the construction of expression vectors to express the OsMADS1 or rice MADS box sequences (or homologous sequences). Such vectors may require linking a promoter sequence to the OsMADS1 or rice MADS box sequence. A number of promoters which are active in plant cells have been described in the literature. Promoters which are known or are found to cause transcription of RNA in plant cells can be used in the present invention. Such promoters may be obtained from plants or viruses and include, but are not limited to, the CaMV 35S promoter. It is preferred that the particular promoter selected should be capable of causing sufficient expression to result in the production of an effective amount of the OsMADS1 gene or MADS box sequence to alter the plant phenotype. The amount of RNA needed to alter the plant phenotype may vary with the plant type and the level of phenotypic change desired. Accordingly, while the 35S promoter is used in the examples presented herein, it should be understood that this promoter may not be the optimal one for all embodiments of the present invention in plants. Furthermore, the promoters used in the DNA constructs of the invention may be modified, if desired, to affect their control characteristics. DNA sequences have been identified which confer regulatory specificity on promoter regions. For example, the small subunit of the ribulose bis-phosphate carboxylase (ss RUBISCO) gene is expressed in plant leaves but not in root tissues. A sequence motif that represses the expression of the ss RUBISCO gene in the absence of light, to create a promoter which is active in leaves but not in root tissue, has been identified. This and/or other regulatory sequence motifs may be ligated to promoters such as the CaMV 35S promoter to modify the expression patterns of a gene. Chimeric promoters so constructed may be used as described herein.

The 3' nontranslated region of genes which are known or are found to function as polyadenylation sites for RNA in plant cells can be used in the present invention. Such 3' nontranslated regions include, but are not limited to, the 3' transcribed, nontranslated region of the CaMV 35S gene and the 3' transcribed, nontranslated regions containing the polyadenylation signals of the tumor-inducing (TI) genes of Agrobacterium, such as the tumor morphology large (tml) gene.

Using the above techniques, the expression vectors containing the OsMADS1 gene sequence or fragments or variants or mutants thereof can be introduced into rice (particularly *O. sativa*) cells, plant cells from other species or non-plant cells as desired.

A DNA construct in accordance with the present invention is introduced, via a suitable vector and transformation method as described below, into plant cells and plants transformed with the introduced DNA are regenerated. Various methods exist for transforming plant cells and thereby generating transgenic plants. Methods which are known or are found to be suitable for creating stably transformed plants can be used in this invention. The choice of method will vary with the type of plant to be transformed; those skilled in the art will recognize the suitability of particular methods for given plant types. Suitable methods may include, but are not limited to: electroporation of plant protoplasts; liposome mediated transformation; polyethylene mediated transformation; transformation using viruses; microinjection of plant cells; microprojectile bombardment of plant cells and *Agrobacterium tumefaciens* (AT) mediated transformation.

It will be obvious to one skilled in the art that a range of suitable vectors for plant transformation is available; the selection of a suitable vector will depend on the transformation technique selected. Suitable vectors are known in the art and some are available on a commercial basis from Clontech (Palo Alto, Calif.) and Pharmacia LKB (Pleasant Hill, Calif.) and other sources.

Examples of particular plant transformation vectors, methods of plant cell transformation and regeneration of transgenic plants are provided in U.S. Pat. No. 5,283,184.

All publications cited herein are incorporated by reference to the same extent as if each individual publication was specifically and individually indicated to be incorporated by reference. The invention now being fully described, it will be apparent to one of ordinary skill in the art that many changes and modifications can be made thereto without departing from the spirit or scope of the claims.

REFERENCES

1. An G, Ebert P R, Mitra A, Ha S B: Binary vectors. In: Gelvin S B, Schilperoort R A (eds) Plant Molecular Biology Manual, pp. A3/1–19. Kluwer Academic, Dordrecht, Belgium (1988).
2. Angenent G C, Busscher M, Franken J, Mol J N M, van Tunen A J: Differential expression of two MADS box genes in wild-type and mutant petunia flowers. Plant Cell 4: 983–993 (1992).
3. Benfey P N, Chua N-H: The cauliflower mosaic virus 35S promoter: combinatorial regulation of transcription in plants. Science 250: 959–966 (1990).
4. Bradley D, Carpenter R, Sommer H, Hartley N, Coen E: Complementary floral homeotic phenotypes result from opposite orientations of a transposon at the *plena locus* of Antirrhinum. Cell 72: 85–95 (1993).
5. Coen E S: The role of homeotic genes in flower development and evolution. Annu. Rev. Plant Physiol. Plant Mol Biol 42: 241–279 (1991).
6. Coen E S, Romero J M, Doyle S, Elliott R, Murphy G, Carpenter R: floricaula: A homeotic gene required for flower development in Antirrhinum majus. Cell 63: 1311–1322 (1990).
7. Cox K H, Goldberg R B: Analysis of plant gene expression. In: Shaw C H (ed) Plant Molecular Biology: A Practical Approach, IRL Press, Oxford (1988) pp. 1–34.
8. Gasser C S: Molecular studies on the differentiation of floral organs. Annu. Rev. Plant Physiol. Plant Mol. Biol. 42: 621–649 (1991).
9. Hoekema A, Hirsch P R, Hooykaas P J J, Schilperoort R A: A binary vector strategy based on separation of vir- and T-region of the *Agrobacterium tumefaciens* Ti-plasmid. Nature 303: 179–181 (1983).
10. Huijser P W, Klein J, Lonnig W-E, Meijer H, Saedler H, Sommer H: Bracteomania, an inflorescence anomaly, is caused by the loss of function of the MADS-box gene squamosa in *Antirrhinum majus*. EMBO J 11; 1239–1249 (1992).
11. Jack T, Brochman L L, Meyerowitz E M: The homeotic gene APETALA3 of *Arabidopsis thaliana* encodes a MADS box and is expressed in petals and stamens. Cell 68:683–697 (1992).
12. Kempin S A, Mandel M A, Yanofsky M F: Conversion of perianth into reproductive organs by ectopic expression of the tobacco floral homeotic gene NAG1. Plant Physiol 103: 1041–1046 (1993).
13. Ma H, Yanofsky M F, Meyerowitz E M: AGL1-AGL6, an Arabidopsis gene family with similarity to floral homeotic and transcription factor genes. Genes Dev 5: 484–495 (1991).
14. Mandel M A, Bowman J L, Kempin S A, Ma H, Meyerowitz E M, Yanofsky M F: Manipulation of floral structure in transgenic tobacco. Cell 71: 133–143 (1992).
15. Mandel M A, Gustafson-Brown C, Savidge B, Yanofsky M F: Molecular characterization of the Arabidopsis floral homeotic gene APETALA1. Nature 360: 273–277 (1992).
16. Mizukami Y, Ma H: Ectopic expression of the floral homeotic gene AGAMOUS in transgenic Arabidopsis plants alters floral organ identity. Cell 71: 119–131 (1992).
17. Pnueli L, Abu-Abeid M, Zamir D, Nacken W, Schwarz-Sommer A, Lifschitz E: The MADS box gene family in tomato: temporal expression during floral development, converted secondary structures and homology with homeotic genes from Antirrhinum and Arabidopsis. Plant J 1: 255–266 (1991).
18. Pnueli L, Hareven D, Broday L, Lifschitz E: The TM5 MADS box gene mediates organ differentiation in three inner whorls of tomato flowers. Plant Cell 6: 175–186 (1994).
19. Pnueli L, Hareven D, Rounsley S D, Yanofsky M F, Lifschitz E: Isolation of the tomato AGAMOUS gene TAG1 and analysis of its homeotic role in transgenic plants. Plant Cell 6: 163–173 (1994).
20. Rogers S O, Bendich A J: Extraction of DNA from plant tissues. In: Gelvin S B, Schilperoort R A (eds) Plant 20. Molecular Manual, pp. A6: 1–10. Kluwer Academic Pub., Dordrecht, Netherlands (1988).
21. Sambrook J, Fritsch E F, Maniatis T: Molecular Cloning: A Laboratory Manual. Cold Spring Harbor Laboratory Press, Cold Spring Harbor, N.Y. (1989).
22. Sanger F, Nicklen S, Coulson A R: DNA sequencing with chain terminating inhibitors. Proc. Natl. Acad. Sci. USA 74: 5463–5467 (1977).
23. Schmidt R J, Velt B, Mandel M A, Mena M, Hake S, Yanofsky M F: Identification and molecular characterization of ZAG1, the maize homologue of the Arabidopsis floral homeotic gene AGAMOUS. Plant Cell 5: 729–737 (1993).
24. Schwarz-Sommer Z, Hue I, Huijser P, Flor P J, Hansen R, Tetens F, Lonnig W-E, Saedler H, Sommer H: Characterization of the Antirrhinum floral homeotic MADS-box gene deficiens: evidence for DNA binding and autoregulation of its persistent expression through flower development. EMBO J 11: 251–263 (1992).
25. Sommer H, Beltran J-P, Huijser P, Pape H, Lonnig W-E, Saedler H, Schwarz-Sommer Z; Deficiens, a homeotic gene involved in the control of flower morphogenesis in *Antirrhinum majus*: the protein shows homology to transcription factors. EMBO J 9: 605–613 (1990).
26. Tamas I A, Hormonal regulation of apical dominance. In: Davies P J (ed) Plant Hormones and their role in plant growth and development, pp. 393–410. Martinus Nijhoff Pub., Dordrecht, Netherlands (1987).
27. Trobner W, Ramirez L, Motte P, Hue I, Huijser P, Lonnig W-E, Saedler H, Sommer H, Schwarz-Sommer Z: GLOBOSA: a homeotic gene which interacts with DEFICIENS in the control of Antirrhinum floral organogenesis. EMBO J 11: 4693–4704 (1992).
28. Tsuchimoto S, van der Krol A R, Chua N-H: Ectopic expression of pMADS3 in transgenic petunia phenocopies the petunia blind mutant. Plant Cell 5: 843–853 (1993).
29. Weigel D, Alvarez J, Smyth D R, Yanofsky M F, Meyerowitz E M: LEAFY controls floral meristem identity in Arabidopsis. Cell 69: 843–859 (1992).
30. Yanofsky M F, Ma H, Bowman J L, Drews G N, Feldmann K A, Meyerowitz E M: The protein encoded by the Arabidopsis homeotic gene agamous resembles transcription factors. Nature 346; 35–39 (1990).

Ahmad et al. (1986). *J. Virol.* 57:267.
Amann and Brosius (1985). *Gene* 40:183.
Alt et al. (1978). *J. Biol. Chem.* 253:1357.
Ausubel et al. (1987). In *Current Protocols in Molecular Biology*, Greene Publishing Associates and Wiley-Intersciences.
Belt et al. (1989). *Gene* 84:407–417.
Bentley et al. (1992). *Genomics* 12:534–541.
Berger et al. (1980). *Cancer Genet. Cytogenet.* 2:259–267.
Bernstein et al. (1985). *Gen. Engr'g* 7:235.
Bolton and McCarthy (1962). *Proc. Natl. Acad. Sci. USA* 48:1390.
Bonner et al. (1973). *J. Mol. Biol.* 81:123.
Boyd et al. (1990). *Genetics* 125:813–819.
Bradley et al. (1988). *BioTechniques* 6:114–116.
Brash et al. (1987). *Mol. Cell Biol.* 7:2013.
Breathnach and Chambon (1981). *Ann. Rev. Biochem.* 50:349–383.
Burke et al. (1987). *Science* 236:806–812.
Caskey (1989). *Science* 236:1223–1228.
Cervenka et al. (1981). *Pediatrics* 67:119–127.
Chamberlain et al. (1988). *Nucl. Acids Res.* 16:1141–1155 (1988).
Church and Gilbert (1988). *Proc. Natl. Acad. Sci. USA* 81:1991–1995.
Cotton et al. (1985). *Proc. Natl. Acad. Sci. USA* 85:4397–4401.
Eisenberg (1984). *Annu. Rev. Biochem.* 53:595–623.
Engvall (1980). *Enzymol.* 70:419.
Felgner et al. (1987). *Proc. Natl. Acad. Sci USA* 84:7413.
Fisher (1980). *Manual of Clinical Immunology*, ch. 42.
Flavell et al. (1978). *Cell* 15:25.
Gasser and Fraley (1989). *Science* 244:1293.
Gebeyehu et al. (1987). *Nucleic Acids Res.* 15:4513–4534.
Geever et al. (1981). *Proc. Natl. Acad. Sci USA* 78:5081.
Glade and Broder (1971). In *In Vitro Methods in Cell Mediated Immunity* 561–570, Bloom, B. R. and Glade, P. R. (eds.), Academic Press, New York.
Glanz and Fraser (1982). *J. Med. Genet.* 19:412–416.
Gluzman (1981). *Cell* 23:175–182.
Gordon-Smith and Rutherford (1991). *Sem. In Hemat.* 28:104–112.
Gorman et al. (1982). *Proc. Natl. Acad. Sci USA* 78:6777–6781.
Graham and vander Eb (1973). *Virology* 52:466.
Gray et al. (1982). *Proc. Natl. Acad. Sci. USA* 79:6598.
Green et al. (1989). *EMBO J.* 8:1067–1072.
Groger et al. (1989). *Gene* 81:285–294.
Harlow and Lane (1988). *Antibodies, A Laboratory Manual*, Cold Spring Harbor Laboratory, New York.
Harper and Saunders (1981). *Chromosoma* 83:431–439.
Innis et al. (1990). *PCR Protocols, A Guide to Methods and Applications*, Innis et al. (eds.), Academic Press, Inc., San Diego, Calif.
Jaspers et al. (1988). *Cytogenet. Cell Genet.* 49:259–263.
Kawasaki et al. (1990). In *PCR Protocols, A Guide to Methods and Applications*, Innis et al. (eds.), 21–27, Academic Press, Inc., San Diego, Calif.
Klein et al. (1987). *Nature* 327:70.
Kohler and Milstein (1975). *Nature* 256:495.
Kozak (1987). *Nucleic Acids Res.* 15:8125–8148.
Kriegler (1990). In *Gene Transfer and Expression*, 131–132, Stockton Press, New York.
Landegren et al. (1989). *Science* 242:229–237.
Landegren et al. (1988). *Science* 241:1077.
Lee et al. (1982). *Nature* 294:228.
Leeder et al. (1989). *Anal. Biochem.* 177:364–372.
Lin et al. (1985). *Cytogenet. Cell Genet.* 39:269–274.
Liu et al. (1992). *Am. J. Hum. Genet.* 51:A55.
Mann et al. (1991). *Genomics* 9:329–337.
Margolskee et al. (1988). *Mol. Cell. Biol.* 8:2837–2847.
McCabe (1990). In *PCR Protocols, A Guide to Methods and Applications*, Innis et al. (eds.), 76–83, Academic Press, New York.
McCuthan et al. (1968). *J. Natl Cancer Inst.* 41:351.
McIntosh et al. (1979). *Am. J. Pediatr. Hematol. Oncol.* 1:107–110.
McLaughlin et al. (1988). *J. Virol.* 62:1963.
Monaco and Lehrach (1991). *Proc. Natl. Acad. Sci. U.S.A.* 88:4123–4127.
Montandon et al. (1989). *Nucleic Acids Res.* 9:3347–3358.
Moss et al. (1987). *Annu. Rev. Immunol.* 5:305.
Moustacchi et al. (1987). *Hum. Genet.* 75:45–47.
Mueller et al. (1978). *Cell* 15:579.
Mulligan and Berg (1981). *Proc. Natl. Acad. Sci. USA* 78:2072–2076.
Mulligan et al. (1981). *Proc. Natl. Acad. Sci. USA* 78:1078∝2076.
Myers and Maniatis (1986). *Cold Spring Harbor Symp. Quant. Biol.* 51:275–284.

Myers et al. (1985). *Science* 230:1242.
Nagamine et al. (1989). *Am. J. Hum. Genet.* 45:337–339.
Nakamura et al. (1987). *Science* 235:1616–1622.
Neumann et al. (1982). *EMBO J* 1:841.
Orita et al. (1989). *Genomics* 5:874–879.
Orkin et al. (1988). *Prog. Med. Genet.* 7:130.
Ouchterlony et al. (1973). In *Handbook of Experimental Immunology,* Wier, D. (ed.) chapter 19. Blackwell.
Petridon and Barrett (1990). *Acta Pardiatr. Scand.* 79:1069–1074.
Proudfoot (1991). *Cell* 64:671–674.
Pursel et al. (1989). *Science* 244:1281–1288.
Rasmussen et al. (1987). *Methods Enzymol.* 139:642.
Riley et al. (1990). *Nucleic Acids Res.* 18:2887–2890.
Roberts et al. (1992). *Genomics* 13:942–950.
Rosenberg et al. (1990). *N. Engl. J. Med.* 323:570–578.
Rousset et al. (1990). *Cancer Res.* 50:2443–2448.
Ruther and Muller-Hill (1983). *EMBO J.* 2:1791.
Saiki et al. (1989). *Proc. Nat. Acad. Sci. USA* 86:6230–6234.
Sambrook et al. (1989). In *Molecular Cloning: A Laboratory Manual,* Cold Spring Harbor, New York.
Sanford et al. (1987). *Particulate Sci. Technol.* 5:27–37.
Sanger et al. (1977). *Proc. Natl. Acad. Sci. U.S.A.* 74:5463.
Santerre et al. (1984). *Gene* 30:147–156.
Sarver et al. (1981). *Mol. Cell Biol.* 1:486.
Schafner (1980). *Proc. Natl. Acad. Sci. USA* 77:2163–2167.
Schroeder et al. (1976). *Hum. Genet.* 32:257–288.
Schroeder et al. (1964). *Hum. Genet.* 1:194–196.
Shapiro and Senapathy (1987). *Nucleic Acids Res.* 15:7155–7174.
Shimatake and Rosenberg (1981). *Nature* (London) 292:128.
Southern (1975). *J. Mol. Biol.* 98:503.
Southern and Berg (1982). *J. Mol. Appl. Genet.* 1:327–341.
Spaete et al. (1982). *Cell* 30:295.
Stanley and Luzio (1984). *EMBO J.* 3:1429.
Stanners et al. (1971). *Nature New Biology* 230:52–54.
Stoflet et al. (1988). *Science* 239:491–494.
Studiar and Moffatt (1986). *J. Mol. Biol.* 189:113.
Sugden et al. (1985). *Mol. Cell Biol.* 5:410.
Summers and Smith (1985). In *Genetically Altered Viruses and the Environment,* Fields et al. (Eds.) 22:319–328, Cold Spring Harbor Laboratory Press, Cold Spring Harbor, N.Y.
Swift (1971). *Nature* 230:370–373.
Tanaka et al. (1989). *Proc. Natl. Acad. Sci. USA* 86:5512–5516.
Tang et al. (1992). *Nature* (London) 356:152–154.
Timberlake and Marshall (1989). *Science* 244:1313–1317.
Trezise and Buchwald (1991). *Nature* 353:434–437.
Tsui and Estevill (1991). In *Genes and Phenotypes* 1–36, Cold Spring Harbor Laboratory Press, Cold Spring Harbor, N.Y.
Vaitukaitis et al. (1971). *J. Clin. Endocrinol. Metab.* 33:988–991.
Van Duuren (1969). *Ann. N.Y. Acad. Sci.* 163:633–651.
Veres et al. (1987). *Science* 237:415–417.
Vermeulen et al. (1991). *Mutation Res.* 255:201–208.
Wallace et al. (1986). *Cold Spring Harbor Symp. Quant. Biol.* 51:257–261.
Ward and Langer et al. (1981). *Proc. Natl. Acad. Sci. USA* 78:6633–6657.
Winship, P. R. (1989). *Nucleic Acids Res.* 17:1266.
Wong et al. (1987). *Nature* 330:384–386.
Wrichnik et al. (1987). *Nucleic Acids Res.* 15:529–542.

TABLE 1

Comparison of phenotypes of transgenic plants with non-transformed control. Seeds were collected from selfed fruits of the primary transgenic plants (T0 generation). The seeds were germinated in a peat pellet and grown for two weeks at 16 h light/8 h dark cycles under fluorescent light. These T1 plants were grown under greenhouse conditions. Ten to twenty plants were analyzed for each transgenic line. Standard errors are shown in parentheses. Progenies carrying the transgenes were identified by visually scoring T2 seedlings for kanamycin resistance. The kanamycin sensitive segregants were used as controls (C). Days to flowering include the time from seed germination to the first anthesis. Height and internode length were measured when fruits were fully developed (90 days postgermination).

| Transgenic line (#) | Days to flowering | Height (cm) | Internode length (cm) |
| --- | --- | --- | --- |
| 1 | 53.0(2.0) | 61.2(5.8) | 5.7(0.5) |
| 2 | 54.2(0.3) | 47.6(1.9) | 4.6(0.2) |
| 3 | 53.0(0.4) | 64.3(3.5) | 5.8(0.3) |
| 7 | 50.6(0.9) | 40.2(4.4) | 3.5(0.3) |
| C | 61.0(0.2) | 119.8(2.2) | 9.0(0.3) |

DETAILED DESCRIPTION OF THE DRAWINGS

FIG. 1. (A) Nucleotide and deduced amino acid sequences of OsMADS1 cDNA. MADS box and K box regions are underlined. The positions of nucleotides and amino acids are shown on the left and right, respectively. (B) Comparison of MADS box regions. Alignment of OsMADS1 (residues 2–57) with other MADS box proteins; AP1, SQUA, AG, PLE, AP3, DEF A. The asterisks indicate identical amino acid to OsMADS1.

FIG. 2. Southern blot analysis of rice DNA probed with the OsMADS1 cDNA. DNA was digested with Eco RI (E), Hind III (H), or Bam HI, fractionated on a 0.7% agarose gel, and hybridized with a probe prepared from the entire cDNA (A) or a probe lacking the conserved MADS box region. The position of Hind III digested lambda DNA size markers are also indicated.

FIG. 3. Northern blot analysis of OsMADS1 transcript in rice. (A) OsMADS1 expression pattern in rice organs. Total RNAs isolated from leaf (L) and root (R) of two-week-old seedlings, and anther (A), carpel (C), and palea/lemma (P) of anthesis-stage flowers were hybridized with the OsMADS1 probe lacking the MADS domain. Ethidium bromide staining of 25S and 18S rRNAs demonstrates equal amounts of RNA loading. (B) Temporal expression pattern during flower development. Total RNA isolated from rice flowers at different developmental stages was used for detection of OsMADS1 gene expression. 1, young inflorescence (panicle size<1 cm), 2, young flower (panicle size=1 to 6 cm); 3, flower at the early vacuolated pollen stage; 4, flower at the late vacuolated pollen stage. Ten µg (samples in Figure A) or 20 µg (samples in Figure B) of total RNA was used.

FIG. 4. Localization of the OsMADS1 transcript in rice flower and phenotypes of transgenic tobacco plants expressing OsMADS1. Expression of OsMADS1 RNA was studied by in situ hybridization experiments using longitudinal sections of young inflorescence (A), and cross sections of upper (B) and lower (C) rice flower at vacuolated pollen stage. Eight µm sections were hybridized with $^{35}$S-labeled antisense RNA which is lacking the MADS box domain. The sections were coated with an X-ray emulsion film and exposed for four days. The samples were stained with 0.5% toluidine blue to visualize tissue sections which show negative expression of the gene. A sense probe did not show any hybridization above the background level. A, anther; F, filament; FP, flower primordia; L, lemma: O, ovary; P, palea; S, sheath; SL, sterile lemma. (D) Comparison of OsMADS1 transgenic plant #7 (left) and wild-type SR1 tobacco (right). (E) A close-up picture of OsMADS1 transgenic plant #2 showing branching and bush phenotypes.

Figure 5:
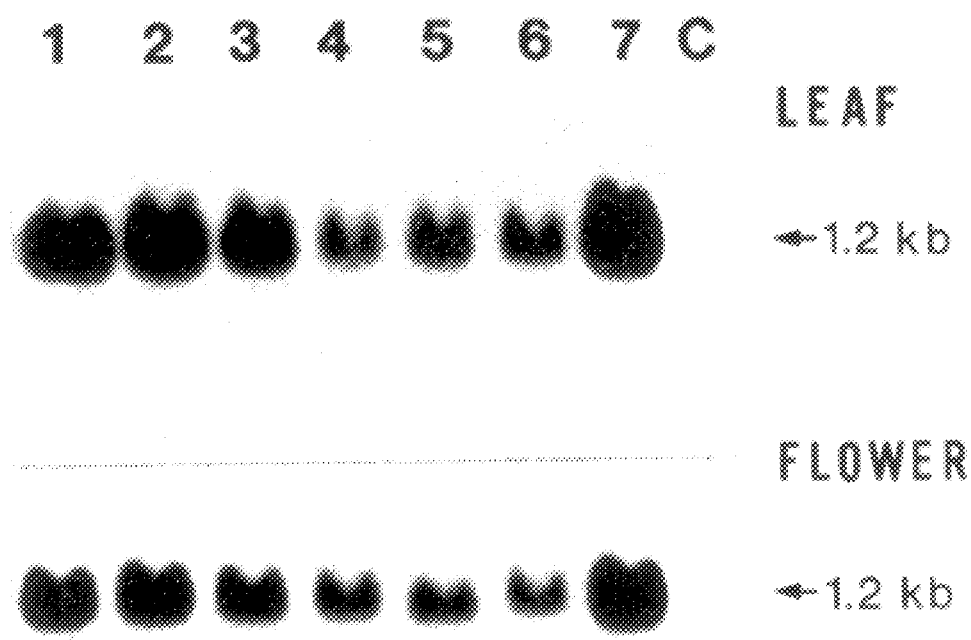
FIG. 5 shows Northern blot analysis of OsMADS1 transcript in transgenic tobacco.

FIG. 5. Northern blot analysis of OsMADS1 transcript in transgenic tobacco. A control plant (C) and seven different transgenic plants (1–7) exhibiting the early flowering and dwarf phenotypes were sampled for preparation of total RNA from leaves and flowers. Twenty µg of total RNA was hybridized with $^{32}$P-labeled probe prepared from the OsMADS1 cDNA lacking the MADS domain.

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 1141 base pairs
        ( B ) TYPE: nucleic acid
        ( C ) STRANDEDNESS: double stranded
        ( D ) TOPOLOGY: linear ( i x ) FEATURE:
        ( A ) NAME/KEY: MADS box
        ( B ) LOCATION: Residues 2-57 of deduced amino acid
            sequence of SEQ ID NO: 1:
        ( C ) IDENTIFICATION METHOD: Homology to MADS-box proteins
            FEATURE:
        ( A ) NAME/KEY: K-Box
        ( B ) LOCATION: Residues 90-143 of deduced amino acid
            sequence of SEQ ID NO: 1:
        ( C ) IDENTIFICATION METHOD: Homology to MADS-box proteins ( x i ) SEQUENCE DESCRIPTION: SEQ ID NO:1:

```
AAAACTAGCT  TGCAAAGGGG  ATAGAGTAGT  AGAGAGAGAG  AGAGAGGAGA  GGAGGAGGAA         60

GAAG                                                                          64

ATG  GGG  AGG  GGG  AAG  GTG  GAG  CTG  AAG  CGG  ATC  GAG  AAC  AAG  ATC  AGC    112
Met  Gly  Arg  Gly  Lys  Val  Glu  Leu  Lys  Arg  Ile  Glu  Asn  Lys  Ile  Ser
 1              5                        10                       15

CGG  CAG  GTG  ACG  TTC  GCC  AAG  CGC  AGG  AAC  GGC  CTG  CTC  AAG  AAG  GCC    160
Arg  Gln  Val  Thr  Phe  Ala  Lys  Arg  Arg  Asn  Gly  Leu  Leu  Lys  Lys  Ala
               20                        25                       30

TAC  GAG  CTC  TCC  CTC  CTC  TGC  GAC  GCC  GAG  GTC  GCC  CTC  ATC  ATC  TTC    208
Tyr  Glu  Leu  Ser  Leu  Leu  Cys  Asp  Ala  Glu  Val  Ala  Leu  Ile  Ile  Phe
          35                        40                       45

TCC  GGC  CGC  GGC  CGC  CTC  TTC  GAG  TTC  TCC  AGC  TCA  TCA  TGC  ATG  TAC    256
Ser  Gly  Arg  Gly  Arg  Leu  Phe  Glu  Phe  Ser  Ser  Ser  Ser  Cys  Met  Tyr
     50                        55                       60

AAA  ACC  TTG  GAG  AGG  TAC  CGC  AGC  TGC  AAC  TAC  AAC  TCA  CAG  GAT  GCA    304
Lys  Thr  Leu  Glu  Arg  Tyr  Arg  Ser  Cys  Asn  Tyr  Asn  Ser  Gln  Asp  Ala
 65                    70                       75                       80

GCA  GCT  CCA  GAA  AAC  GAA  ATT  AAT  TAC  CAA  GAA  TAC  CTG  AAG  CTG  AAA    352
Ala  Ala  Pro  Glu  Asn  Glu  Ile  Asn  Tyr  Gln  Glu  Tyr  Leu  Lys  Leu  Lys
                    85                       90                       95

ACA  AGA  GTT  GAA  TTT  CTT  CAA  ACC  ACA  CAG  AGA  AAT  ATT  CTT  GGT  GAG    400
Thr  Arg  Val  Glu  Phe  Leu  Gln  Thr  Thr  Gln  Arg  Asn  Ile  Leu  Gly  Glu
               100                      105                     110

GAT  TTG  GGC  CCA  CTA  AGC  ATG  AAG  GAG  CTG  GAG  CAG  CTT  GAG  AAC  CAG    448
Asp  Leu  Gly  Pro  Leu  Ser  Met  Lys  Glu  Leu  Glu  Gln  Leu  Glu  Asn  Gln
          115                      120                     125

ATA  GAA  GTA  TCC  CTC  AAA  CAA  ATC  AGG  TCA  AGA  AAG  AAC  CAA  GCA  CTG    496
Ile  Glu  Val  Ser  Leu  Lys  Gln  Ile  Arg  Ser  Arg  Lys  Asn  Gln  Ala  Leu
     130                     135                     140

CTT  GAT  CAG  CTG  TTT  GAT  CTG  AAG  AGC  AAG  GAG  CAA  CAG  CTG  CAA  GAT    544
```

```
Leu  Asp  Gln  Leu  Phe  Asp  Leu  Lys  Ser  Lys  Glu  Gln  Gln  Leu  Gln  Asp
145                      150                      155                      160

CTC  AAC  AAA  GAC  TTG  AGG  AAA  AAG  TTA  CAG  GAA  ACC  AGT  GCA  GAG  AAT     592
Leu  Asn  Lys  Asp  Leu  Arg  Lys  Lys  Leu  Gln  Glu  Thr  Ser  Ala  Glu  Asn
                    165                      170                      175

GTG  CTC  CAT  ATG  TCC  TGG  CAA  GAT  GGT  GGT  GGG  CAC  AGC  GGT  TCT  AGC     640
Val  Leu  His  Met  Ser  Trp  Gln  Asp  Gly  Gly  Gly  His  Ser  Gly  Ser  Ser
               180                      185                      190

ACT  GTT  CTT  GCT  GAT  CAG  CCT  CAT  CAC  CAT  CAG  GGT  CTT  CTC  CAC  CCT     688
Thr  Val  Leu  Ala  Asp  Gln  Pro  His  His  His  Gln  Gly  Leu  Leu  His  Pro
          195                      200                      205

CAC  CCA  GAT  CAG  GGT  GAC  CAT  TCC  CTG  CAG  ATT  GGG  TAT  CAT  CAC  CCT     736
His  Pro  Asp  Gln  Gly  Asp  His  Ser  Leu  Gln  Ile  Gly  Tyr  His  His  Pro
     210                      215                      220

CAT  GCT  CAC  CAT  CAC  CAG  GCC  TAC  ATG  GAC  CAT  CTG  AGC  AAT  GAA  GCA     784
His  Ala  His  His  His  Gln  Ala  Tyr  Met  Asp  His  Leu  Ser  Asn  Glu  Ala
225                      230                      235                      240

GCA  GAC  ATG  GTT  GCT  CAT  CAC  CCC  AAT  GAA  CAC  ATC  CCA  TCC  GGC  TGG     832
Ala  Asp  Met  Val  Ala  His  His  Pro  Asn  Glu  His  Ile  Pro  Ser  Gly  Trp
                    245                      250                      255

ATA  TGA                                                                            838
Ile

TGTGTGTGTT    CAGTTCAGGC    TTCAGGCTTC    AGAGAAGCCA    ATGCAAACAG    TGTCCTGTAA    898

TCCAGTAATT    ACAGGGCATA    TGTAATGTAA    TGTAATGTAA    TCCCTGATCT    ATATTTTGCT    958

AAGTACGTGC    GTGCTCTCTT    ACGACCTTCT    CCCCCAAACA    GTTAATCAGG    GGAATAATAA    1018

TTTCGTTTGA    TGCACGTACT    GTATGTCTGT    ATCTGTCACT    GTATCGTAGG    ACCGTCCATG    1078

TATAACAATT    TCCGTTTTGG    ATGTGGTAAC    AATTAATTGG    CACTTAAATT    TATATTTGTG    1138

ATG                                                                                 1141
```

( 2 ) INFORMATION FOR SEQ ID NO: 2:

( i ) SEQUENCE CHARACTERISTICS:
        ( A ) LENGTH: 56 amino acids
        ( B ) TYPE: amino acid (deduced)
        ( D ) TOPOLOGY: linear ( i x ) FEATURE:
        ( A ) NAME/KEY: Homology with AP1, SQUA, AG, PLE, AP3,
            DEFA
        ( B ) LOCATION: Amino acids 1- 56
        ( C ) IDENTIFICATION METHOD: Amino acid sequence homology
        ( D ) OTHER INFORMATION: MADS-box region of SEQ ID NO:1,
            amino acids 2-57

( x i ) SEQUENCE DESCRIPTION: SEQ ID NO:2:

```
Gly  Arg  Gly  Lys  Val  Glu  Leu  Lys  Arg  Ile  Glu  Asn  Lys  Ile  Ser  Arg
                    5                        10                       15

Gln  Val  Thr  Phe  Ala  Lys  Arg  Arg  Asn  Gly  Leu  Leu  Lys  Lys  Ala  Tyr
               20                       25                       30

Glu  Leu  Ser  Leu  Leu  Cys  Asp  Ala  Glu  Val  Ala  Leu  Ile  Ile  Phe  Ser
          35                       40                       45

Gly  Arg  Gly  Arg  Leu  Phe  Glu  Phe
          50                   55
```

( 2 ) INFORMATION FOR SEQ ID NO: 3:

( i ) SEQUENCE CHARACTERISTICS:
        ( A ) LENGTH: 56 amino acids
        ( B ) TYPE: amino acid (deduced)
        ( D ) TOPOLOGY: linear ( i x ) FEATURE:
        ( A ) NAME/KEY: Homology with SEQ ID NO:2

(B) LOCATION: Amino acids 1-56
        (C) IDENTIFICATION METHOD: Amino acid sequence homology
        (D) OTHER INFORMATION: MADS-box region of AP1

(xi) SEQUENCE DESCRIPTION: SEQ ID NO:3:

Gly Arg Gly Arg Val Gln Leu Lys Arg Ile Glu Asn Lys Ile Asn Arg
                 5                   10                  15

Gln Val Thr Phe Ser Lys Arg Arg Ala Gly Leu Leu Lys Lys Ala His
                20                  25                  30

Glu Ile Ser Val Leu Cys Asp Ala Glu Val Ala Leu Val Val Phe Ser
            35                  40              45

His Lys Gly Lys Leu Phe Glu Tyr
    50                  55

(2) INFORMATION FOR SEQ ID NO: 4:

(i) SEQUENCE CHARACTERISTICS:
        (A) LENGTH: 56 amino acids
        (B) TYPE: amino acid
        (D) TOPOLOGY: linear (ix) FEATURE:
        (A) NAME/KEY: Homology with SEQ ID NO:2
        (B) LOCATION: Amino acids 1-56
        (C) IDENTIFICATION METHOD: Amino acid sequence homology
        (D) OTHER INFORMATION: MADS-box region of SQUA (xi) SEQUENCE DESCRIPTION: SEQ ID NO:4:

Gly Arg Gly Lys Val Gln Leu Lys Arg Ile Glu Asn Lys Ile Asn Arg
                 5                   10                  15

Gln Val Thr Phe Ser Lys Arg Arg Gly Gly Leu Leu Lys Lys Ala His
                20                  25                  30

Glu Leu Ser Val Leu Cys Asp Ala Glu Val Ala Leu Ile Val Phe Ser
            35                  40              45

Asn Lys Gly Lys Leu Phe Glu Tyr
    50                  55

(2) INFORMATION FOR SEQ ID NO: 5:

(i) SEQUENCE CHARACTERISTICS:
        (A) LENGTH: 56 amino acids
        (B) TYPE: amino acid
        (D) TOPOLOGY: linear (ix) FEATURE:
        (A) NAME/KEY: Homology with SEQ ID NO:2
        (B) LOCATION: Amino acids 1-56
        (C) IDENTIFICATION METHOD: Amino acid sequence homology
        (D) OTHER INFORMATION: MADS-box region of AG (xi) SEQUENCE DESCRIPTION: SEQ ID NO:5:

Gly Arg Gly Lys Ile Glu Ile Lys Arg Ile Glu Asn Thr Thr Asn Arg
                 5                   10                  15

Gln Val Thr Phe Cys Lys Arg Arg Asn Gly Leu Leu Lys Lys Ala Tyr
                20                  25                  30

Glu Leu Ser Val Leu Cys Asp Ala Glu Val Ala Leu Ile Val Phe Ser
            35                  40              45

Ser Arg Gly Arg Leu Tyr Glu Tyr
    50                  55

(2) INFORMATION FOR SEQ ID NO: 6:

(i) SEQUENCE CHARACTERISTICS:
        (A) LENGTH: 56 amino acid residues
        (B) TYPE: amino acid
        (D) TOPOLOGY: linear (ix) FEATURE:

(A) NAME/KEY: Homology with SEQ ID NO:2
            (B) LOCATION: Amino acids 1- 56
            (C) IDENTIFICATION METHOD: Amino acid sequence homology
            (D) OTHER INFORMATION: MADS-box region of PLE (xi) SEQUENCE DESCRIPTION: SEQ ID NO:6:

Gly Arg Gly Lys Ile Glu Ile Lys Arg Ile Glu Asn Ile Thr Asn Arg
                5               10                  15

Gln Val Thr Phe Cys Lys Arg Arg Asn Gly Leu Leu Lys Lys Ala Tyr
                20              25                  30

Glu Leu Ser Val Leu Cys Asp Ala Glu Val Ala Leu Val Val Phe Ser
            35              40              45

Ser Arg Gly Arg Leu Tyr Glu Tyr
        50              55

(2) INFORMATION FOR SEQ ID NO: 7:

(i) SEQUENCE CHARACTERISTICS:
        (A) LENGTH: 56 amino acids
        (B) TYPE: amino acid
        (D) TOPOLOGY: linear (ix) FEATURE:
        (A) NAME/KEY: Homology with SEQ ID NO:2
        (B) LOCATION: Amino acids 1- 56
        (C) IDENTIFICATION METHOD: Amino acid sequence homology
        (D) OTHER INFORMATION: MADS-box region of AP3

(xi) SEQUENCE DESCRIPTION: SEQ ID NO:7:

Gly Gly Gly Arg Val Gln Leu Lys Arg Ile Glu Asn Gln Thr Asn Arg
                5               10                  15

Gln Val Thr Tyr Ser Lys Arg Arg Asn Gly Leu Phe Lys Lys Ala His
                20              25                  30

Glu Leu Thr Val Leu Cys Asp Ala Arg Val Ser Ile Ile Met Phe Ser
            35              40              45

Ser Ser Asn Lys Leu His Glu Tyr
        50              55

(2) INFORMATION FOR SEQ ID NO: 8:

(i) SEQUENCE CHARACTERISTICS:
        (A) LENGTH: 56 amino acid residues
        (B) TYPE: amino acid (deduced)
        (D) TOPOLOGY: linear (ix) FEATURE:
        (A) NAME/KEY: Homology with SEQ ID NO:2
        (B) LOCATION: Amino acids 1- 56
        (C) IDENTIFICATION METHOD: Amino acid sequence homology
        (D) OTHER INFORMATION: MADS-box region of DEFA (xi) SEQUENCE DESCRIPTION: SEQ ID NO:8:

Ala Arg Gly Lys Ile Gln Ile Lys Arg Ile Glu Asn Gln Thr Asn Arg
                5               10                  15

Gln Val Thr Tyr Ser Lys Arg Arg Asn Gly Leu Phe Lys Lys Ala His
                20              25                  30

Glu Leu Ser Val Leu Cys Asp Ala Lys Val Ser Ile Ile Met Ile Ser
            35              40              45

Ser Thr Gln Lys Leu His Glu Tyr
        50              55

I claim:

1. An isolated polynucleotide comprising a sequence selected from the group consisting of:
(a) a sequence of at least 30 consecutive nucleotides of SEQ ID NO:1;
(b) a sequence of at least 100 nucleotides having at least 70% nucleotide sequence similarity with SEQ ID NO:1, not including MADS-1 box and K-box regions of SEQ ID NO:1;
(c) the OsMADS1 MADS-box sequence; and (d) the OsMADS1 K-box sequence.

2. The polynucleotide of claim 1 comprising at least 30 consecutive nucleotides of SEQ ID NO:1.

3. The polynucleotide of claim 2 comprising the OsMADS1 polypeptide-coding region of SEQ ID NO:1.

4. The polynucleotide of claim 2 comprising the sequence shown in SEQ ID NO:1.

5. A vector comprising the polynucleotide of claim 2.

6. A cell comprising the polynucleotide of claim 2.

7. A transgenic plant comprising the polynucleotide of claim 2.

8. The polynucleotide of claim 1 comprising a sequence of greater than 100 nucleotides having at least 70% nucleotide sequence similarity with SEQ ID NO:1, not including the MADS-1 box and K-box regions of SEO ID NO:1.

9. The polynucleotide of claim 8 comprising a sequence of at least 100 nucleotides having at least 80% nucleotide sequence similarity with SEQ ID NO:1, not including the MADS-1 box and K-box regions of SEQ ID NO:1.

10. The polynucleotide of claim 8 comprising a sequence of greater than 100 nucleotides having at least 90% nucleotide sequence similarity with SEQ ID NO:1 , not including the MADS-1 box and K-box regions of SEO ID NO:1.

11. The polynucleotide of claim 8 wherein expression of said polynucleotide in a transgenic plant results in one or more phenotypes selected from the group consisting of altered floral organ development, early flowering, reduced apical dominance, and dwarfing.

12. The polynucleotide of claim 8 encoding at least a portion of the OsMADS1 polypeptide or a polypeptide having only silent or conservative substitutions to said portion.

13. The polynucleotide of claim 8 encoding at least a portion of the OsMADS1 polypeptide.

14. The polynucleotide of claim 13 comprising a member of the group consisting of the OsMADS1 MADS-box sequence and the OsMADS1 K-box sequence.

15. A vector comprising the polynucleotide of claim 8.

16. A cell comprising the polynucleotide of claim 8.

17. A transgenic plant comprising the polynucleotide of claim 8.

18. The polynucleotide of claim 1 comprising at least one member of the group consisting of the OsMADS1 MADS-box sequence and the OsMADS1 K-box sequence.

19. A vector comprising the polynucleotide of claim 18.

20. A cell comprising the polynucleotide of claim 18.

21. A transgenic plant comprising the polynucleotide of claim 18.

22. A method of making a transgenic plant comprising the steps of:

introducing the polynucleotide of claim 2 into a plant cell, thereby producing a transformed plant cell; and producing a transgenic plant from the transformed plant cell.

23. A method of making a transgenic plant comprising the steps of:

introducing the polynucleotide of claim 8 into a plant cell, thereby producing a transformed plant cell; and producing a transgenic plant from the transformed plant cell.

24. A method of making a transgenic plant comprising the steps of:

introducing the polynucleotide of claim 18 into a plant cell, thereby producing a transformed plant cell; and producing a transgenic plant from the transformed plant cell.

* * * * *

UNITED STATES PATENT AND TRADEMARK OFFICE
CERTIFICATE OF CORRECTION

PATENT NO. : 5,859,326
DATED : January 12, 1999
INVENTOR(S) : Gynheung An

It is certified that error appears in the above-identified patent and that said Letters Patent is hereby corrected as shown below:

Title page,
Item [56], References Cited, Publications, second column, "Coen et al., "floricaula: A Homeotic Gene Required for Flower Development in *Antirrhinum majus,* "O Cell 63: 1311-1322 (1990)" should be -- Coen et al., "floricaula: A Homeotic Gene Required for Flower Development in *Antirrhinum majus,*" *Cell 63:*1311-1322 (1990) --.

Column 2,
Line 34, "(lacZ,)M15/recA1." should be -- (lacZ)M15/recA1, --.

Column 3,
Line 7, "SQE ID" should be -- SEQ ID --.

Column 4,
Line 34, a period -- . -- should be inserted after "*gene*" and before "The".

Column 7,
Line 19, the comma "," after "and " and before "the" should be deleted.

Column 9,
Line 31, "Asn" should be -- Lys --, and "Ser" should be -- Arg --.

Column 18,
Lines 64 and 65, "Mulligan et al. (1981). *Proc. Natl. Acad. Sci. USA 78:*1078∝2076" should be -- Mulligan et al. (1981). *Proc. Natl. Acad. Sci. USA 78:*1078∝2076 --.

UNITED STATES PATENT AND TRADEMARK OFFICE
CERTIFICATE OF CORRECTION

PATENT NO. : 5,859,326
DATED : January 12, 1999
INVENTOR(S) : Gynheung An

It is certified that error appears in the above-identified patent and that said Letters Patent is hereby corrected as shown below:

Claims,

Column 28, claim 1,
Line 65, "MADS-1 box" should be -- MADS-box --.

Column 29, claim 8,
Line 15, "MADS-1 box" should be -- MADS-box --; and "SEO ID" should be -- SEQ ID --.

Column 29, claim 9,
Line 19, claim 9, "MADS-1 box" should be -- MADS-box --.

Column 29, claim 10,
Line 23, "MADS-1 box" should be -- MADS-box; and "SEO ID" should be -- SEQ ID --.

Signed and Sealed this

Ninth Day of October, 2001

*Attest:*

NICHOLAS P. GODICI
*Attesting Officer*     *Acting Director of the United States Patent and Trademark Office*